United States Patent
Ryan et al.

(10) Patent No.: US 9,011,528 B2
(45) Date of Patent: Apr. 21, 2015

(54) FLEXIBLE ANNULOPLASTY PROSTHESIS

(75) Inventors: Timothy R. Ryan, Shorewood, MN (US); Charles P. Tabor, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1750 days.

(21) Appl. No.: 11/411,274

(22) Filed: Apr. 26, 2006

(65) Prior Publication Data

US 2007/0191939 A1    Aug. 16, 2007

Related U.S. Application Data

(60) Provisional application No. 60/722,793, filed on Sep. 30, 2005.

(51) Int. Cl.
*A61F 2/24* (2006.01)

(52) U.S. Cl.
CPC .............. *A61F 2/2445* (2013.01); *A61F 2/2442* (2013.01); *A61F 2220/0075* (2013.01); *A61F 2230/0019* (2013.01); *A61F 2250/0098* (2013.01); *A61F 2210/0076* (2013.01)

(58) Field of Classification Search
CPC ... A61F 2/2409; A61F 2/2442; A61F 2/2445; A61F 2/2448; A61F 2/0063
USPC ..................... 623/2.36–2.41, 23.72
See application file for complete search history.

(56) References Cited

U.S. PATENT DOCUMENTS

| 755,921 | A | 3/1904 | O'Neill |
|---|---|---|---|
| 1,452,372 | A | 4/1923 | Gomez |
| 3,409,013 | A | 11/1968 | Berry |
| 3,656,185 | A | 4/1972 | Carpentier |
| 3,746,002 | A | 7/1973 | Haller |
| 3,828,787 | A | 8/1974 | Anderson et al. |
| 4,042,979 | A | 8/1977 | Angell |
| 4,055,861 | A | 11/1977 | Carpentier et al. |
| 4,106,129 | A | 8/1978 | Carpentier et al. |
| 4,164,046 | A * | 8/1979 | Cooley .......................... 623/2.36 |

(Continued)

FOREIGN PATENT DOCUMENTS

| GB | 2083362 | 2/1982 |
|---|---|---|
| GB | 2108393 | 5/1983 |

(Continued)

OTHER PUBLICATIONS

Surgical Techniques for the Repair of Anterior Mitral Leaflet Prolapse / Carlos M.G. Duran, M.D., Ph.D. / J Card Surg 1999; 14:471-481.

(Continued)

*Primary Examiner* — Thomas J Sweet
*Assistant Examiner* — Cheryl Miller

(57) ABSTRACT

A flexible annuloplasty prosthesis for repairing a heart valve having a valve annulus. The annuloplasty prosthesis comprises a flexible body defining an exterior of the prosthesis formed of a biocompatible material and configured to rest against and support the heart valve annulus upon implantation. The flexible annuloplasty prosthesis has a height of not more than 2.5 mm. This low profile characteristic enhances a surgeon's ability to implant the prosthesis. In one preferred embodiment, the flexible body is a fabric material folded onto itself along a length thereof, with the annuloplasty prosthesis being characterized by an elevated longitudinal stiffness.

19 Claims, 9 Drawing Sheets

(56) References Cited

U.S. PATENT DOCUMENTS

| | | | |
|---|---|---|---|
| 4,185,636 A | | 1/1980 | Gabbay |
| 4,204,283 A | | 5/1980 | Bellhouse et al. |
| 4,217,665 A | * | 8/1980 | Bex et al. ............... 623/2.36 |
| 4,290,151 A | | 9/1981 | Massana |
| 4,306,319 A | | 12/1981 | Kaster |
| 4,366,581 A | * | 1/1983 | Shah ..................... 623/2.41 |
| 4,535,483 A | * | 8/1985 | Klawitter et al. .......... 623/2.4 |
| 4,612,011 A | | 9/1986 | Kaultzky |
| 4,648,401 A | | 3/1987 | Matson |
| 4,655,218 A | | 4/1987 | Kulik et al. |
| 4,702,250 A | | 10/1987 | Ovil et al. |
| 4,743,253 A | | 5/1988 | Magladry |
| 4,755,181 A | | 7/1988 | Igoe |
| 4,865,600 A | | 9/1989 | Carpentier et al. |
| 4,911,064 A | | 3/1990 | Roth |
| 4,932,965 A | | 6/1990 | Phillips |
| 5,011,481 A | | 4/1991 | Myers et al. |
| 5,041,130 A | | 8/1991 | Cosgrove et al. |
| 5,059,198 A | | 10/1991 | Gimpelson |
| 5,059,214 A | | 10/1991 | Akopov et al. |
| 5,071,428 A | | 12/1991 | Chin et al. |
| 5,104,407 A | | 4/1992 | Lam et al. |
| 5,197,979 A | | 3/1993 | Quintero et al. |
| 5,201,739 A | | 4/1993 | Semm |
| 5,211,655 A | | 5/1993 | Hasson |
| 5,217,460 A | | 6/1993 | Knoepfler |
| 5,241,968 A | | 9/1993 | Slater |
| 5,290,300 A | | 3/1994 | Cosgrove et al. |
| 5,306,296 A | | 4/1994 | Wright et al. |
| 5,350,420 A | | 9/1994 | Cosgrove et al. |
| 5,383,886 A | | 1/1995 | Kensey et al. |
| 5,415,667 A | | 5/1995 | Frater |
| 5,496,336 A | | 3/1996 | Cosgrove et al. |
| 5,522,884 A | | 6/1996 | Wright |
| 5,638,402 A | | 6/1997 | Osaka et al. |
| 5,674,279 A | * | 10/1997 | Wright et al. ............ 623/2.37 |
| 5,752,972 A | | 5/1998 | Hoogeboom |
| 5,843,178 A | * | 12/1998 | Vanney et al. ............ 623/2.36 |
| 5,984,959 A | | 11/1999 | Robertson et al. |
| 6,159,240 A | | 12/2000 | Sparer et al. |
| 6,174,332 B1 | * | 1/2001 | Loch et al. ............... 623/2.37 |
| 6,183,512 B1 | | 2/2001 | Howanee, Jr. et al. |
| 6,231,602 B1 | * | 5/2001 | Carpentier et al. ....... 623/2.36 |
| 6,283,993 B1 | | 9/2001 | Cosgrove et al. |
| 6,319,280 B1 | | 11/2001 | Schoon |
| 6,332,893 B1 | | 12/2001 | Mortier et al. |
| 6,402,780 B2 | * | 6/2002 | Williamson et al. ....... 623/2.11 |
| 6,406,492 B1 | | 6/2002 | Lytle |
| 6,409,758 B2 | | 6/2002 | Stobie et al. |
| 6,558,416 B2 | | 5/2003 | Cosgrove et al. |
| 6,702,852 B2 | | 3/2004 | Stobie et al. |
| 6,719,786 B2 | | 4/2004 | Ryan et al. |
| 6,786,924 B2 | | 9/2004 | Ryan et al. |
| 6,955,689 B2 | | 10/2005 | Ryan et al. |
| 8,267,993 B2 | * | 9/2012 | Nguyen et al. ............ 623/2.11 |
| 8,500,798 B2 | * | 8/2013 | Rowe et al. ............... 623/2.1 |
| 2001/0044656 A1 | * | 11/2001 | Williamson et al. ....... 623/2.11 |
| 2001/0049558 A1 | | 12/2001 | Liddicoat et al. |
| 2002/0129820 A1 | | 9/2002 | Ryan et al. |
| 2002/0188350 A1 | * | 12/2002 | Arru et al. ............... 623/2.36 |
| 2003/0176917 A1 | | 9/2003 | Ryan et al. |
| 2003/0195620 A1 | * | 10/2003 | Huynh et al. ............ 623/2.14 |
| 2003/0204250 A1 | * | 10/2003 | Bicer ..................... 623/2.4 |
| 2004/0006384 A1 | | 1/2004 | McCarthy |
| 2004/0019357 A1 | | 1/2004 | Campbell et al. |
| 2004/0024451 A1 | | 2/2004 | Johnson et al. |
| 2004/0148018 A1 | * | 7/2004 | Carpentier et al. ........ 623/2.18 |
| 2005/0065597 A1 | * | 3/2005 | Lansac ................... 623/2.11 |
| 2005/0197696 A1 | | 9/2005 | Duran |
| 2005/0256567 A1 | * | 11/2005 | Lim et al. ............... 623/2.36 |
| 2006/0206203 A1 | * | 9/2006 | Yang et al. .............. 623/2.37 |

FOREIGN PATENT DOCUMENTS

| | | |
|---|---|---|
| SU | 878285 | 11/1981 |
| WO | WO 00/59408 | 10/2000 |
| WO | 2004/041099 | 5/2004 |
| WO | 2005/055883 | 6/2005 |

OTHER PUBLICATIONS

Medtronic Booklet "Medtronic Duran Flexible Annuloplasty Systems In-Service Guide" / UC200004685 EN, (2000).

Carpentier-Edwards Physio Annuloplasty Ring, "Technical Product Manual," Baxter (1996) (22 pages).

Ian J. Reece, M.B., F.R.C.S., et al., "Surgical Treatment of Mitral Systolic Click Syndrome: Results in 37 Patients," The Annuals of Thoracic Surgery, vol. 39, No. 2, Feb. 1985 (pp. 155-158).

Denton A. Cooley, M.D., et al., "Mitral Leaflet Prolapse: Surgical Treatment using a Posterior Annular Collar Prosthesis," Cardiovascular Diseases, Bulletin of the Texas Heart Institute, vol. 3, Nov. 4, 1976 (pp. 438-439; 442-443).

Ormiston, et al., "Size and Motion in the Mitral Valve Annulus in Man," Circulation (1981) 64:113.

Dagum, et al., "Potential Mechanism of Left Ventricular Outflow Tract Obstruction After Mitral Ring Annuloplasty," J. Thorac. Cardiovasc. Surg. (1999) 117:472-80.

David, et al., "Left Ventricular Function After Mitral Valve Surgery," J. Heart Dis. (1995) 4:S175-80.

Duran, "Perspectives for Acquired Valvular Disease," Advanced Cardiac Surgery (1993) vol. 4.

Okada, et al., "Comparison of the Carpentier and Duran Prosthetic Rings Used in Mitral Reconstruction," Ann. Thorac. Surg. (1995) 59:658-63.

Duran, et al., "Clinical and Hemodynamic Performance of a Totally Flexible Prosthetic Ring for Atrio-Ventricular Valve Reconstruction," Ann. Thorac. Surg. (1976) 22:458-63.

Van Rijk-zwikker, et al., "Comparison to Flexible Rings for Annuloplasty of the Mitral Valve," Circulation (1990) 82 (Suppl. IV):IV 58-64.

* cited by examiner

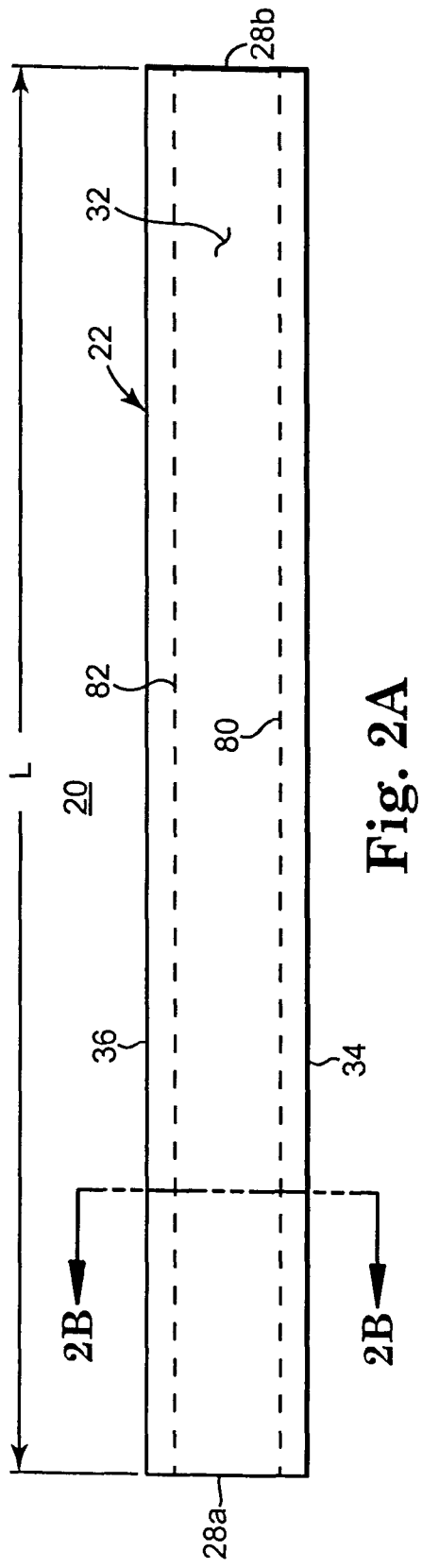
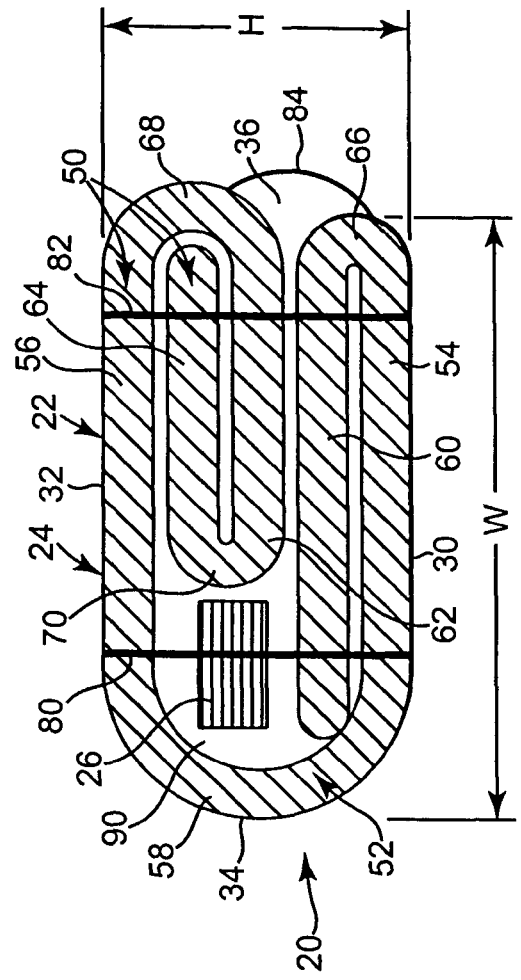
Fig. 2A
Fig. 2B

FLEXIBLE ANNULOPLASTY PROSTHESIS

CROSS-REFERENCE TO RELATED APPLICATIONS

This application claims the benefit under §119(e)(1), and incorporates herein by reference an entirety of, U.S. Provisional Application No. 60/722,793, filed Sep. 30, 2005 and entitled "Flexible Annuloplasty Prosthesis."

BACKGROUND OF THE INVENTION

The present invention relates generally to annuloplasty prostheses. More particularly, it relates to flexible annuloplasty prostheses for use in conjunction with heart repair procedures, such as annuloplasty bands or rings.

Improvements in cardiopulmonary bypass and myocardial protection and standardization of surgical techniques have lead to increasing interest in valve reconstruction procedures. See, for example, Ormiston J A, Shah P M, Tei C, et al., Size and Motion in the Mitral Valve Annulus in Man, *Circulation* 1981; 64:113; Dagum P, Green G R, Glasson J R, et al., Potential Mechanism of Left Ventricular Outflow Tract Obstruction After Mitral Ring Annuloplasty, *J Thorac Cardiovasc Surg.* 1999; 117:472-80; David T E, Armstrong S, Sun Z, Left Ventricular Function After Mitral Valve Surgery, *J Heart Dis* 1995; 4:S175-80; and Duran C, Perspectives for Acquired Valvular Disease, *Advanced Cardiac Surgery*, Vol. 4, 1993.

As highlighted by the above, annuloplasty bands and rings have been recognized as being highly useful in a variety of surgical procedures, including mitral and tricuspid valve repair. In general terms, valve annuloplasty is an operation that selectively reduces the size of the valve annulus via an implanted prosthetic device (e.g., annuloplasty band or annuloplasty ring). As implied by the name, an "annuloplasty ring" is a continuous body or ring (e.g., circular- or oval-shaped), whereas an "annuloplasty band" is an elongated body having opposed, unconnected ends. With either construction, the annuloplasty prosthesis is typically characterized as being either flexible or rigid. A rigid annuloplasty prosthetic includes one or more internal stiffening members (e.g., a shaped, metal rod) that enables the prosthesis to return to an original shape after an external force is removed, whereas a flexible annuloplasty prosthesis does not.

Commercial embodiments of annuloplasty prosthetic products include the SJM Tailor™ annuloplasty ring and the SJM Seguin™ annuloplasty ring available from St. Jude Medical of Saint Paul, Minn.; the Carpentier-Edwards annuloplasty rings available from Edwards of Irvine, Calif.; and products sold under the Future, Duran, or Ancore™ trade names available from Medtronic, Inc., of Minneapolis, Minn. A prior art system is described in a brochure entitled "Medtronic Duran Flexible Annuloplasty Systems in Service Guide," published by Medtronic, Inc., in 2000, Publication No. UC20004685 EN. In addition, annuloplasty prosthesis and surgical methods for implanting prostheses for addressing heart disorders are described in Okada Y, Shomura T, Yamura Yl, et al., Comparison of the Carpentier and Duran Prosthetic Rings Used in Mitral Reconstruction, *Ann Thorac Surg* 1995; 59:658-63; Duran C M G; Ubago J L M; Clinical and Hemodynamic Performance of a Totally Flexible Prosthetic Ring for Atrio-Ventricular Valve Reconstruction, *Ann Thorac Surg* 1976; 22:458-63; and Van Rijk-zwikker G L, Mast F, Shepperheyn J J, et al., Comparison to Flexible Rings for Annuloplasty of the Mitral Valve, *Circulation,* 1990; 82 (Suppl. IV):IV 58-64.

Rigid and flexible annuloplasty prostheses each present certain advantages as possible disadvantages. For example, flexible annuloplasty prostheses can more readily conform to the particular shape and contour of the heart valve annulus being repaired as compared to a rigid product. However, in order to sufficiently support the heart valve annulus being repaired, flexible annuloplasty prostheses are somewhat thicker (e.g., the Duran™ annuloplasty ring and band products have a nominal height or thickness of 3-3.5 mm.)

Additionally, as part of an annuloplasty procedure, surgeons often desire to plicate (i.e., reduce) specific regions of the annulus being repaired. By way of background, implantation of an annuloplasty ring or band includes placing one or more sutures through the annulus tissue, and then coupling or connecting the so-placed suture(s) to the annuloplasty device. A typical suture arrangement entails looping a suture through the annular tissue such that opposing ends or segments of the suture (otherwise extending from the annulus tissue) define a "suture pair". With this in mind, plication of annular tissue is typically accomplished by establishing a decreased spacing between segments of the suture pair along the annuloplasty prosthesis as compared to the suture pair spacing at the annular tissue. For example, a suture pair can be spaced approximately 5-6 mm in width at the annulus and approximately 4 mm in width at the annuloplasty prosthesis. Subsequently, when the annuloplasty device is cinched against the tissue via the suture pair, the prosthetic forces the suture pair to pull (plicate) annular tissue together between the suture segments. This phenomenon is shown schematically in FIG. 1A in which an annuloplasty prosthesis 10 (shown in side view) is initially secured to annular tissue 12 (shown schematically) by a suture pair 14. In FIG. 1B, the prosthesis 10 is moved against the annular tissue 12, with the suture pair 14 being tied at a knot 16 and causing tissue plication (referenced at 18). Forces exerted by the suture pair 14 on the annular tissue 12 are represented by arrows. Notably, because the suture pair 14 must be tightly bound in order to maintain the tissue plication, tying of the suture pair 14 via the knot 16 also imparts a longitudinally compressive force on the annuloplasty prosthesis 10 as well. Known flexible annuloplasty products, such as flexible annuloplasty bands or rings, have limited longitudinal stiffness, such that when a longitudinal force is applied thereto, the prosthetic may readily buckle or deform along regions subjected to this compressive force as shown in FIG. 1C. A similar phenomena is also observed in non-plicating applications (e.g., simply securing/tying down the suture knot can cause buckling). While the above-described buckling does not appear to negatively affect the efficacy of the implanted device, surgeons may be concerned with the buckled appearance.

SUMMARY

In one aspect, the present invention generally is directed toward a novel, flexible annuloplasty prosthesis. The prosthesis has a low profile as compared to prior art devices, thus giving rise to attendant advantages. It may also, in some embodiments, be characterized as longitudinally stiffer than prior art flexible annuloplasty devices.

In one embodiment, a flexible annuloplasty prosthesis for repairing a heart valve having a valve annulus is provided. The annuloplasty prosthesis comprises a flexible body defining an exterior of the prosthesis formed of a biocompatible material and configured to rest against and support the heart valve annulus upon implantation. In this regard, the flexible annuloplasty prosthesis has a height of not more than 2.5 mm. As compared to known flexible prostheses, this low profile characteristic of one aspect of the present invention enhances a surgeon's ability to implant the prosthetic. In one preferred embodiment, the flexible body is a fabric material folded onto itself along a length thereof, with the annuloplasty prosthesis characterized by the absence of a stiffening member within the fabric.

In another embodiment, a flexible annuloplasty prosthesis for repairing a heart valve having a valve annulus is provided. The annuloplasty prosthesis includes a flexible, fabric material body folded onto itself along a length thereof to define an exterior surface of the annuloplasty prosthesis. Further, the annuloplasty prosthesis has a height of not more than 2.5 mm, a width of not more than 4.75 mm, a substantially rectangular shape in transverse cross-section, and exhibits a Force-Displacement Slope Average Value of not less than 10 lbs/in over the first 1 mm of compression. In one preferred embodiment, the flexible annuloplasty prosthesis is a band; in another preferred embodiment, the annuloplasty prosthesis is a ring.

BRIEF DESCRIPTION OF THE DRAWINGS

FIG. 2A is a top view of an embodiment of a flexible annuloplasty prosthesis in accordance with principles of the present invention;

FIG. 2B is a transverse cross-sectional view of the annuloplasty prosthesis of FIG. 2A, taken along the lines B-B;

DETAILED DESCRIPTION

Figure 1A:
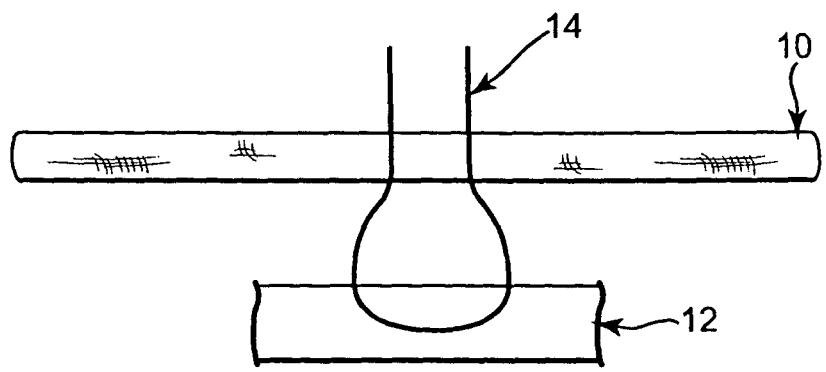
FIGS. 1A and 1B are schematic side views of a flexible annuloplasty prosthesis being secured to annular tissue with a suture pair.
Figure 1B:
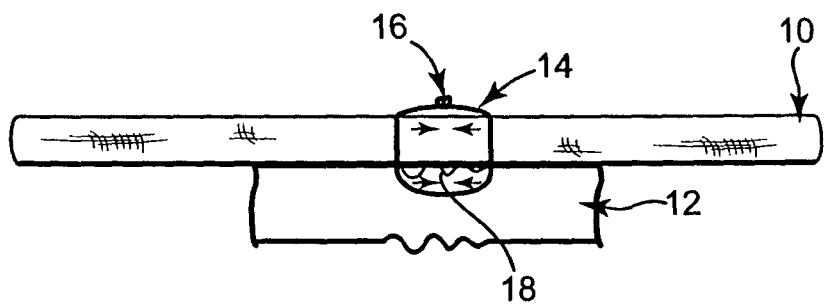
Figure 1C:
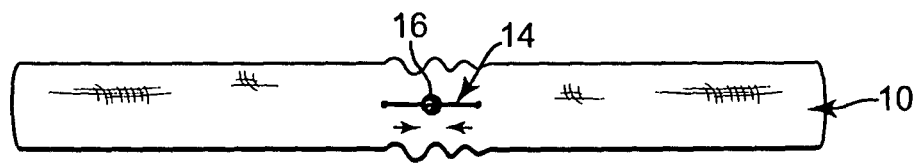
FIG. 1C is a schematic, top view of a prior art flexible annuloplasty prosthesis subjected to the forces arising from the arrangement of FIG. 1C.

One embodiment of a flexible annuloplasty prosthesis 20 in accordance with aspects of the present invention is shown in FIGS. 2A and 2B. The annuloplasty prosthesis 20 includes a flexible body 22 defining an exterior surface 24 (referenced generally in FIG. 2B) of the prosthesis 20. In one embodiment, the annuloplasty prosthesis 20 further includes a marker 26 (FIG. 2B). Details on these components are provided below. In general terms, the annuloplasty prosthesis 20 has a reduced profile as compared to prior art flexible annuloplasty designs, and exhibits elevated longitudinal stiffness in some embodiments. Regardless, while the annuloplasty prosthesis 20 is shown in FIG. 2A as being an annuloplasty band (with discrete, unconnected ends 28a, 28b), in alternative embodiments, the prosthesis 20 is provided as a ring (such that discernable ends are not formed).

The flexible body 22 is formed of a biocompatible material. As used herein, the term "flexible body" specifically excludes tissue. In one embodiment, the flexible body 22 is formed of a cloth or fabric material folded onto itself along a length thereof as shown in FIG. 2B. One appropriate fabric material for use as the flexible body 22 is a polyester double velour material. For example, in one embodiment, the flexible body 22 is comprised of a polyester velour material available under the trade designation Advantage 166611 Meadox double velour from Boston Scientific of Boston, Mass. Another exemplary velour material is available under the trade designation M04057 from Bard Peripheral Vascular of C.R. Bard, Inc., of Murray Hill, N.J. Alternatively, the flexible body 22 material can be a variety of other polymeric or metallic materials, or combinations thereof. Other suitable materials include, but are not limited to, polypropylene, cellulose, polyvinyl, silicone, polytetrafluoroethylene, Silastic, carbon-fiber, polyethylene, nylon, polyester, etc. The material may be knitted, woven, sprayed, molded, cast, extruded, or punched from a blank.

Regardless of the selected material, the flexible body 22 is formed to define one or more folds that in turn effectively define two or more layers in transverse cross-section (FIG. 2A). By way of reference, the annuloplasty prosthesis 20 can be described as defining opposing, first and second major surfaces 30, 32 (best shown in FIG. 2A), and opposing sides 34, 36 (referenced generally). Where the annuloplasty prosthesis 20 is provided as a band, the annuloplasty prosthesis 20 is further defined by the opposing, first and second ends 28a, 28b (FIG. 2A). Alternatively, where the annuloplasty prosthesis 20 is a ring, a continuous body is formed. Upon implantation, one of the first or second major surfaces 30, 32 is placed against and intimately contacts annular tissue (not shown) such that a height H (or thickness) of the annuloplasty prosthesis 20 is defined as a dimension between the major surfaces 30, 32. Conversely, a width W of the annuloplasty prosthesis 20 is defined as a dimension between the first and second sides 34, 36, while a length L is defined as a dimension between the ends 28a, 28b. With these conventions in mind, the flexible body 22 is, in one embodiment, folded to form, along the length L and in transverse cross-section, a plurality of layers 50 (referenced generally) and at least one fold segment 52 (referenced generally) interconnecting two of the layers 50. The plurality of layers 50 includes at least a first layer 54 and a second layer 56. The first layer 54 defines the first major surface 30 of the annuloplasty prosthesis 20, whereas the second layer 56 defines the second major surface 32. Further, the first and second layers 54, 56 are interconnected by a first fold segment 58 that otherwise defines the first side 34 of the annuloplasty prosthesis 20.

As described below, a wide variety of fold configurations can be employed in accordance with aspects of the present invention. With the one embodiment of FIG. 2B, however, the flexible body 22 is folded to define, in transverse cross-section, the first and second layers 54, 56, as well as a third layer 60, a fourth layer 62, and a fifth layer 64. The first and second layers 54, 56 are oriented horizontally (relative to the upright position of FIG. 2B) in a substantially parallel fashion (e.g., within 15 degrees of a true parallel relationship). The third layer 60 is positioned between the first and second layers 54, 56, and is oriented in a substantially parallel fashion relative thereto. In one embodiment, the third layer 60 is interconnected with the first layer 54 via a second fold segment 66. The fourth layer 62 is positioned between the second and third layers 56, 60, and is oriented in a substantially parallel fashion thereto. The fourth layer 62 is interconnected with the second layer 56 by a third fold segment 68. Finally, the fifth layer 64 is positioned between the second and fourth layers 56, 62, and is oriented in a substantially parallel fashion thereto. The fifth layer 64 is interconnected with the fourth layer 62 via a fourth fold segment 70.

With the above configuration, the first fold segment 58 defines the first side 34 of the annuloplasty prosthesis 20, whereas the second and third fold segment 66, 68 combine to define the second side 36. The folded configuration of the flexible body 22 (and the substantially parallel relationship between the layers 54, 56, 60-64) is maintained, in one embodiment, by first and second stitch lines 80, 82. The stitch lines 80, 82 serve as hem stitchings, extending through an entire thickness of the flexible body 22, thus retaining the annuloplasty prosthesis 20 to the desired height H as described below. In one embodiment, the stitch lines 80, 82 are formed with sutures (e.g., 4-0 suture material), although other appropriate materials are also acceptable. In one embodiment, the first stitch line 80 is formed adjacent the first fold segment 58, whereas the second stitch line 82 is formed adjacent the second and third fold segments 66, 68. This spaced placement of the stitch lines 80, 82 (e.g., adjacent the first and second sides 34, 36 of the annuloplasty prosthesis 20) ensures that the flexible body 22 retains the substantially rectangular transverse cross-sectional shape shown in FIG. 2B, and thus the desired overall low profile of the annuloplasty prosthesis 20 described below. To further ensure an overall structural integrity of the folded flexible body 22 and/or to identify the seam formed between the second and third fold segments 66, 68, in one embodiment an additional seam stitching 84, such as whipstitches, can be provided that connects the second and third fold segments 66, 68.

The above-described folding of the flexible body 22 generates, in one embodiment, a region 90 within which the marker 26 is received. For example, in one embodiment, the region 90 is defined by a spacing, in transverse cross-section, between the first and fourth fold segments 58, 70, as well as a spacing between the second and third layers 56, 60. With this positioning, the marker 26 can be secured relative to the flexible body 22 via the first stitch line 80. Alternatively, the flexible body 22 can be folded in a variety of other fashions such that the marker 26 is located at a position other than that shown in FIG. 2B. Regardless, the marker 26 is, in one embodiment, a radiopaque marker (e.g., a silicone radiopaque marker) useful for identifying a position of the annuloplasty prosthesis 20 following implantation via non-invasive imaging. The marker 26 does not, in one embodiment, overtly stiffen the annuloplasty prosthesis 20 as would a conventional stiffening member. Thus, the marker 26 is a not a stiffening member (e.g., the marker 26 is not a metal rod), such that annuloplasty prosthesis 20 remains flexible even with the presence of the marker 26. Further, the marker 26 is highly thin (on the order of 0.020 inch in height and 1 mm in width in one embodiment) such that the overall nominal height H and width W of the annuloplasty prosthesis 20 defined by the folded flexible body 22 is not altered by the marker 26.

It has surprisingly been found that the polyester velour material for the flexible body 22 in combination with the folded configuration illustrated in FIG. 2B results in the annuloplasty prosthesis 20 being highly viable for repairing a heart valve annulus (e.g., mitral valve or tricuspid valve) to the same extent as accepted prior art products in that the annuloplasty prosthesis 20 is able to reinforce or alter an annular shape, yet exhibits a lower profile and, in some embodiments, enhanced longitudinal stiffness. Relative to the low profile attribute, the nominal height H of the annuloplasty prosthesis 20 is not more than 2.50 mm, more preferably not more than 2.30 mm. This represents a distinct advancement over known flexible annuloplasty prosthesis products all of which are believed to have a nominal height of at least 3.0 mm (e.g., the Duran™ annuloplasty prosthesis available from Medtronic, Inc., of Minneapolis, Minn. has a measured nominal height on the order of 3-3.5 mm). Thus, during an implantation procedure, the annuloplasty prosthesis 20 in accordance with aspects of the present invention will not overtly interfere with a surgeon's vision of the surgical site. Further, the lower profile attribute more readily promotes desire improved hemodynamics following implant.

This low profile characteristic is, in one embodiment, further enhanced by the substantially rectangular transverse cross-sectional shape of the annuloplasty prosthesis 20. To this end, the phrase "substantially rectangular" is with reference to the general configuration illustrated in FIG. 2B whereby the first and second major surfaces 30, 32 are substantially flat or linear, whereas the first and second sides 34, 36 are generally curved (in alternative embodiments, the sides 34, 36 may also be substantially flat or linear). This substantially rectangular transverse cross-sectional shape is in contrast to prior art annuloplasty products that otherwise have a more circular transverse cross-sectional shape. It has surprisingly been found that the substantially rectangular shape associated with aspects of the present invention enhances a surgeon's ability to identify one or both of the sides 34, 36 of the annuloplasty prosthesis 20, and thus, to more quickly identify desired location for suture placement through the annuloplasty prosthesis 20 during an implantation procedure.

In addition, in one embodiment, the nominal width W is preferably less than 5 mm, more preferably less than 4.5 mm, and even more preferably, between 3.75-4.25 mm. Thus, unlike conventional flexible annuloplasty prostheses, the annuloplasty prosthetic 20 in accordance with aspects of the present invention is characterized by a width W that is greater than a height H.

Finally, by way of reference, where the annuloplasty prosthesis 20 is provided as a band, the annuloplasty prosthesis 20 can have any suitable length L. In one embodiment, the length L of the annuloplasty prosthesis 20 is less than about 400 mm, more preferably less than about 200 mm, and even more preferably about 100 mm. The length L is preferably more than 25 mm.

Figure 2C:
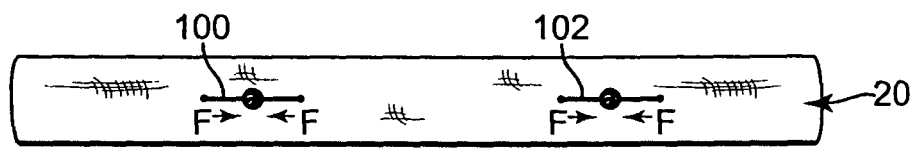
FIG. 2C is a schematic top view of the annuloplasty prosthesis of FIG. 2A, illustrating longitudinal forces normally encountered during implantation.

In addition to the dimensional and shape characteristics described above, the annuloplasty prosthesis 20 is, in one embodiment, characterized as being longitudinally stiff. The phrase "longitudinally stiff" or "longitudinal stiffness" is with reference to an ability of the annuloplasty prosthesis 20 to resist a longitudinally applied compressive force without buckling or displacement. A "longitudinal compressive force" defined as a force applied to a segment of the annuloplasty prosthesis 20 in a direction substantially parallel with the longitudinal axis thereof. As described above, tying of suture pairs into knots (with or without tissue plication) commonly results in sutures imparting a longitudinal compressive force onto the implanted annuloplasty device. For example, FIG. 2C schematically illustrates the annuloplasty prosthesis 20 in top plan view, with suture pairs 100, 102 (each tightened and secured by a knot, respectively), each exerting longitudinal compressive forces (represented by arrows F) onto the prosthesis 20. The longitudinal stiffness attribute of the annuloplasty prosthesis 20 resists these longitudinal compressive forces, such that the annuloplasty prosthetic 20 in accordance with aspects of the present invention is longitudinally stiff and will not buckle or otherwise deform in the presence of longitudinal compressive forces normally encountered with implantation.

Longitudinal stiffness of the annuloplasty prosthesis 20 in accordance with one embodiment can be characterized by a Force-Displacement Slope Average Value that can be determined by the following method. The annuloplasty prosthesis 20 is secured at the sites to a test fixture employing an Absolute Digimatic Dial Indicator (available from Mitutoyo Corp. of Japan) to create 4.5 mm of exposed product between the two attachment sites. A first one of the attachment sites is incrementally displaced toward the second attachment site to create a compressive force on the annuloplasty prosthesis 20. A force measurement is recorded at each increment of test fixture displacement. The Force-Displacement Slope Average Value of the annuloplasty prosthesis 20 is then determined over the first one millimeter of test fixture displacement. With this definition in mind, the annuloplasty prosthesis 20 in accordance with aspects of the present invention preferably exhibits a Force-Displacement Slope Average Value of not less than 10.0 lbs/in over the first 1 mm of compression; more preferably, not less than 10.5 lbs/in over the first 1 mm of compression; even more preferably, not less than 11.0 lbs/in over the first 1 mm of compression.

The annuloplasty prosthesis 20 described with reference to FIGS. 2A and 2B is but one acceptable configuration in accordance with the present invention. For example, an alternative embodiment, flexible annuloplasty prosthesis 120 is shown in transverse, cross-section in FIG. 3. The annuloplasty prosthesis 120 is highly similar to the annuloplasty prosthesis 20 (FIG. 2B) previously described, and includes a flexible body 122 defining an exterior surface 124 (referenced generally) of the annuloplasty prosthesis 120. In one embodiment, the annuloplasty prosthesis 120 further includes a marker 126 contained within the flexible body 122.

The flexible body 122 can be formed of any of the materials previously described with respect to the flexible body 22 (FIG. 2B), and in one embodiment is a cloth or fabric material (e.g., a double velour material) folded on to itself along a length thereof. In particular, in transverse cross-section, the flexible body 122 is folded to define a first layer 130, a second layer 132, a third layer 134, and a fourth layer 136. The first and second layers 130, 132 are outer layers, and define opposing major surfaces 138, 140 of the annuloplasty prosthesis 120. Further, the first and second layers 130, 132 are oriented in a substantially parallel fashion relative to one another (horizontal in the upright position of FIG. 3), and are interconnected by a first fold segment 142. The third layer 134 is positioned between the first and second layers 130, 132, and is oriented in a substantially parallel fashion thereto. The third layer 134 is interconnected with the first layer 130 via a second fold segment 144. The fourth layer 136 is positioned between the second and third layers 132, 134, and is oriented in a substantially parallel fashion relative thereto. Further, the second and fourth layers 132, 136 are interconnected by a third fold segment 146.

Figure 3:
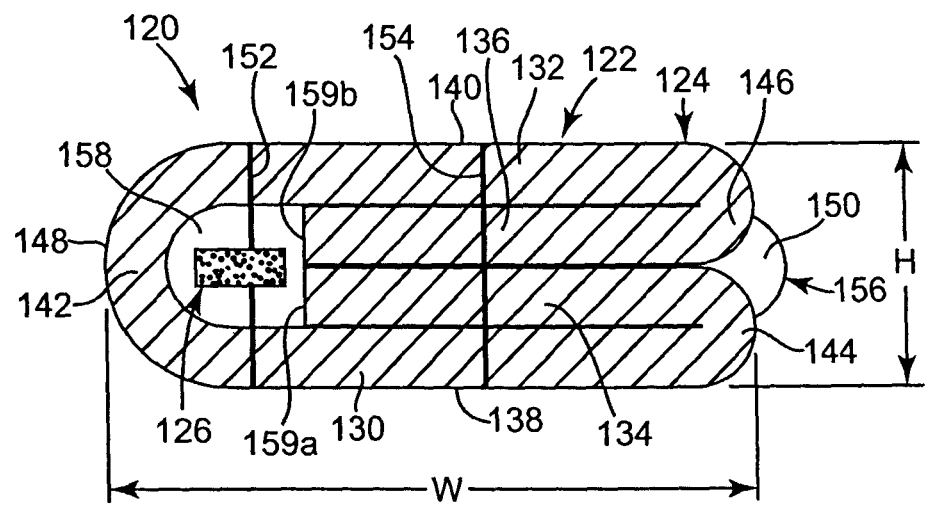
FIG. 3 is a transverse cross-sectional view of another embodiment flexible annuloplasty prosthesis in accordance with principles of the present invention.

As shown in FIG. 3, the folded flexible body 122 defines a substantially rectangular shape in transverse cross-section, with the first fold segment 142 defining a first side 148 of the annuloplasty prosthesis 120, whereas the second and third fold segments 144, 146 combine to define a second side 150 (referenced generally). First and second stitch lines 152, 154 can be employed to retain the flexible body 122 in the folded shape shown in FIG. 4. Additionally, seam stitching 156 identifies a location of a seam formed by the second and third fold segments 144, 146 and/or retains the second and third fold segments 144, 146 relative to one another, although in alternative embodiments can be eliminated. Regardless, the marker 126 is similar to the marker 26 (FIG. 2B) previously described, and is retained within a region 158 established between the first and second layers 130, 132 and between edges 159a, 159b of the third and fourth layers 134, 136, respectively, relative to an interior surface of the first fold segment 142. With this positioning, the first stitch line 152 secures the marker 126 to the flexible body 122. Alternatively, the marker 126 can be located at other positions relative to the flexible body 122, or can be eliminated.

The annuloplasty prosthesis 120 has a nominal height H (defined as a dimension between the major surfaces 138, 140 otherwise formed by the first and second layers 130, 132) of not more than 2.5 mm, more preferably not more than 2.3 mm. In other embodiments, the annuloplasty prosthesis 120 has a nominal width W greater than the height H, with the width W being not more than 5 mm, more preferably not more than 4.5 mm. Finally, the annuloplasty prosthesis 120 is preferably characterized, in one embodiment, by a Force-Displacement Slope Average Value of not less than 10.0 lbs/in over the first 1 mm of compression; more preferably not less than 10.5 lbs/in over the first 1 mm of compression; even more preferably not less than 11.0 lbs/in over the first 1 mm of compression.

Figure 4:
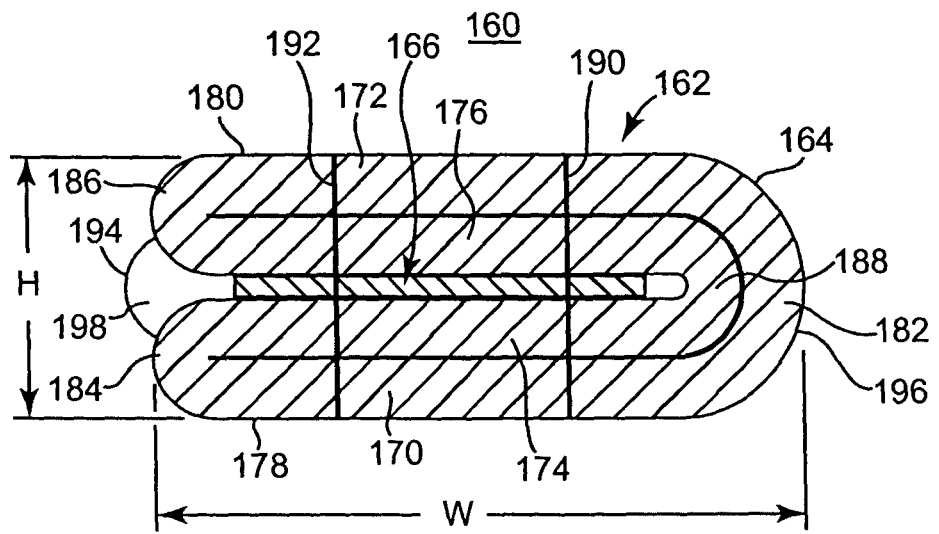
FIG. 4 is a transverse cross-sectional view of another embodiment flexible annuloplasty prosthesis in accordance with principles of the present invention.

Another embodiment flexible annuloplasty prosthesis 160 in accordance with principles of the present invention is shown in transverse cross-section in FIG. 4. The annuloplasty prosthesis 160 includes a flexible body 162 defining an exterior surface 164 (referenced generally) of the annuloplasty prosthesis 160 as well as, in some embodiments, a marker 166.

The flexible body 162 can be made of any of the materials previously described with respect to the flexible body 22 (FIG. 2B), and is preferably a cloth or fabric material (e.g., a double velour material) folded onto itself along a length thereof. As compared to previous embodiments, the flexible body 162 is initially tubular, and is folded to define, in transverse cross-section, first, second, third, and fourth layers 170-176. The first and second layers 170, 172 are outer layers, and define opposing major surfaces 178, 180 of the annuloplasty prosthesis 160. The first and second layers 170, 172 are oriented in a substantially perpendicular fashion, and are interconnected by a first fold segment 182. The third layer 174 is positioned between the first and second layers 170, 172 and is oriented in a substantially parallel fashion relative thereto. The first and third layers 170, 174 are interconnected by a second fold segment 184. The fourth layer 176 is formed between the second and third layers 172, 174, and is oriented in a substantially parallel manner relative thereto. The second and fourth layers 172, 176 are interconnected by a third fold segment 186, whereas the third and fourth layers 174, 176 are interconnected by a fourth fold segment 188. The marker 166 is disposed between the third and fourth layers 174, 176.

As with previous embodiments, the annuloplasty prosthesis 160, and in particular the folded flexible body 162, assumes a substantially rectangular shape in transverse cross-section. One or more stitch lines 190, 192 are employed to retain the flexible body 162 to this folded shape, as well to secure the marker 166 to the flexible body 162. Finally, seam stitching 194 can be provided to interconnect and indicate a location of a seam defined by the third and fourth layers 174, 176. Regardless, the first fold segment 182 defines a first side 196 of the annuloplasty prosthesis 160, whereas the second and fourth fold segments 184, 188 combine to define a second side 198 (referenced generally).

The annuloplasty prosthesis 160 associated with the embodiment of FIG. 4 has a nominal height H (i.e., dimension between the major surfaces 178, 180 otherwise defined by the first and second layers 170, 172) of not more than 2.5 mm, more preferably not more than 2.3 mm. Further, in other embodiments, the annuloplasty prosthesis 160 has a nominal width W greater than the height H, with the nominal width W being not greater than 5.0 mm, more preferably not greater than 4.5 mm. Finally, the annuloplasty prosthesis 160 preferably exhibits a Force-Displacement Slope Average Value of not less than 10.0 lbs/in over the first 1 mm of compression; more preferably not less than 10.5 lbs/in over the first 1 mm of compression; even more preferably not less than 11.0 lbs/in over the first 1 mm of compression.

Figure 5:
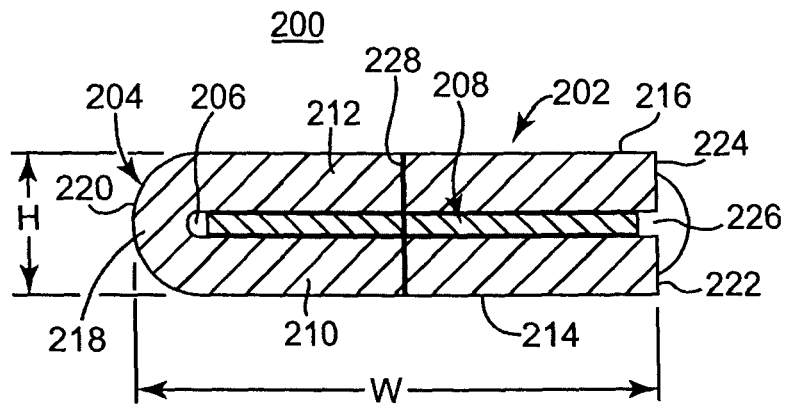
FIG. 5 is a transverse cross-sectional view of another embodiment flexible annuloplasty prosthesis in accordance with principles of the present invention.

Yet another embodiment flexible annuloplasty prosthesis 200 in accordance with principles of the present invention is shown in FIG. 5. The annuloplasty prosthesis 200 is similar to previous embodiments and includes a flexible body 202 defining an exterior surface 204 (referenced generally) of the annuloplasty prosthesis 200. In addition, the annuloplasty prosthesis 200 includes a marker 206 and a support insert 208.

The flexible body 202 can be formed of any of the materials previously described with respect to the flexible body 22 (FIG. 2B), and is preferably a fabric or cloth material (e.g., a double velour material) folded onto itself along a length thereof to define first and second layers 210, 212 in transverse cross-section. By way of reference, the first layer 210 defines a first major surface 214 of the annuloplasty prosthesis 200, whereas the second layer 212 defines a second major surface 216. The first and second layers 210, 212 are interconnected by a fold segment 218 that otherwise defines a first side 220 of the annuloplasty prosthesis 200. With the one embodiment of FIG. 5, the first and second layers 210, 212 terminate in a free edge 222, 224, respectively, that otherwise combine to define a second side 226 (referenced generally) of the annuloplasty prosthesis 200. In one embodiment, the edges 222, 224 are secured to one another via a stitch line 228.

The marker 206 is akin to the marker 26 (FIG. 2B) previously described and is contained within the folded flexible body 202. Though not shown, an additional stitch line can be employed to retain the marker 206 relative to the flexible body 202.

The support insert 208 can be configured to have properties differing from those associated with the materials selected for the flexible body 202. For example, the support insert 208 can be formed to create desired mechanical properties in the annuloplasty prosthesis 200, such as enhanced lateral support when applied to a heart valve annulus (not shown). However, the support insert 208 is not a rigid stiffening member otherwise employed with conventional, rigid, annuloplasty products, such that the annuloplasty prosthesis 200 remains flexible. For example, in one embodiment, the support insert 208 is a woven material, such as woven polyester. Alternatively, the support insert 208 can be a polymeric material.

As with previous embodiments, the annuloplasty prosthesis 200 is configured to adequately support a heart valve annulus (not shown) in a manner commensurate with currently available products, yet has a nominal height H of not more than 2.5 mm, more preferably not more than 2.3 mm. In some embodiments, the annuloplasty prosthesis 200 has a nominal width W greater than the height, with the width W being not more than 5.0 mm, more preferably not more than 4.5 mm. Finally, in some embodiments, the annuloplasty prosthesis 200 preferably exhibits a Force-Displacement Slope Average Value of not less than 10.0 lbs/in over the first 1 mm of compression, more preferably not less than 10.5 lbs/in over the first 1 mm of compression, even more preferably not less than 11.0 lbs/in over the first 1 mm of compression.

Figure 6:
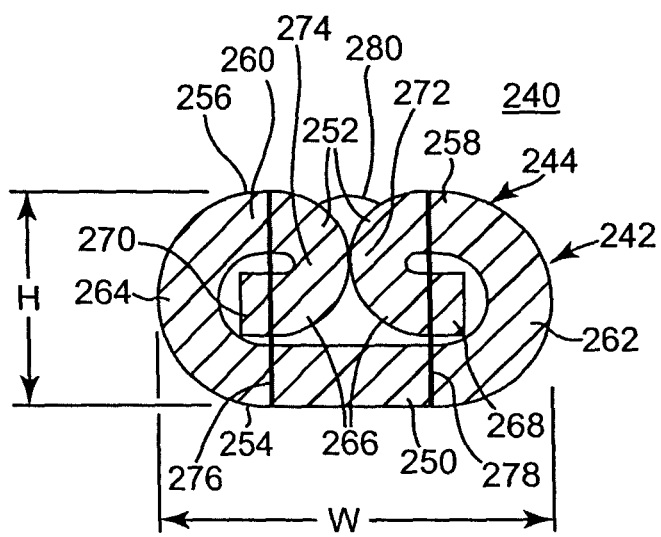
FIG. 6 is a transverse cross-sectional view of another embodiment flexible annuloplasty prosthesis in accordance with principles of the present invention.

Yet another embodiment flexible annuloplasty prosthesis 240 in accordance with principles of the present invention is shown in FIG. 6. The annuloplasty prosthesis 240 is similar to previous embodiments, and includes a flexible body 242 defining an exterior surface 244 (referenced generally) of the annuloplasty prosthesis 240. The flexible body 242 can be formed of any of the material previously described with respect to the flexible body 22 (FIG. 2B), and is preferably a fabric or cloth material (e.g., a double velour material) folded onto itself along a length thereof.

In particular, the flexible body 242 is folded to define, in transverse cross-section, a first layer 250 and a second layer 252 (referenced generally), that in turn define opposing major surfaces 254, 256 of the annuloplasty prosthesis 240. As compared to previous embodiments, the second layer 252 is discontinuous, defined by opposing external portions 258, 260 of the flexible body 242. The first external portion 258 is interconnected with the first layer 250 by a first fold segment 262. Similarly, the second external portion 260 is interconnected with the first layer 250 by a second fold segment 264. Finally, a third layer 266 (reference generally) is defined between the first and second layers 250, 252. The third layer 266 is discontinuous, being defined by opposing first and second internal portions 268, 270. The first internal portion 268 is interconnected with the first external portion 258 via a third fold segment 272. The second internal portion 270 is interconnected with the second external portion 260 by a fourth fold segment 274.

As with previous embodiments, the annuloplasty prosthesis 240 is, in some embodiments, substantially rectangular in transverse cross-section. First and second stitch lines 276, 278 are employed, in one embodiment, to retain the flexible body 242 in the desired shape, as well as to minimize possible unfolding of the flexible body 242. Additionally, in one embodiment, a seam stitch 280 connects the first and second external portions 258, 260, providing a user with an indication of where a seam in the second layer 252 exists. Regardless, the annuloplasty prosthesis 240 has a nominal height H of not more than 2.5 mm, more preferably not more than 2.3 mm. Further, in some embodiments, the annuloplasty prosthesis 240 has a nominal width W greater than the height H and is not greater than 5.0 mm, more preferably not greater than 4.5 mm. Finally, in some embodiments, the annuloplasty prosthesis 240 preferably exhibits a force-displacement slope average value of greater than 10.0 lbs/in over the first 1 mm of compression, not less than 10.5 lbs/in, and even more preferably not less than 11.0 lbs/in.

Figure 7:
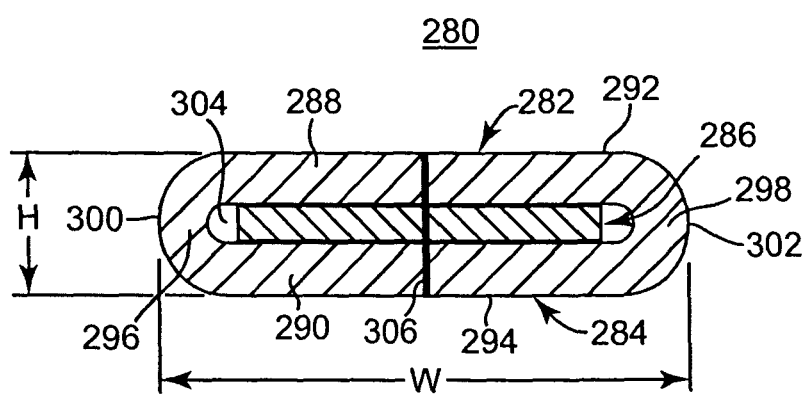
FIG. 7 is a transverse cross-sectional view of another embodiment flexible annuloplasty prosthesis in accordance with principles of the present invention.

Yet another embodiment flexible annuloplasty prosthesis 280 in accordance with principles of the present invention is shown in FIG. 7. The annuloplasty prosthesis 280 is similar to previous embodiments and includes a flexible body 282 defining an exterior surface 284 (referenced generally) of the prosthesis 280. In addition, the annuloplasty prosthesis 280 includes a support insert 286.

The flexible body 282 can be formed of any of the materials previously described with respect to the flexible body 22 (FIG. 2B), and is preferably a fabric or cloth material (e.g., a double velour material). Regardless, the flexible body 282 is tubular such that upon final assembly about the support insert 286, the flexible body 282 defines first and second layer 288, 290 in transverse cross-section. By way of reference, the first layer 288 defines a first major surface 292 of the flexible annuloplasty prosthesis 280, whereas the second layer 290 defines a second major surface 294. Further, upon final assembly, the first and second layers 288, 290 are interconnected by segments 296, 298 that define first and second sides 300, 302, respectively, of the annuloplasty prosthesis 280. Finally, the flexible body 282 forms an interior region 304 within which the support insert 286 is disposed.

The support insert 286 can be configured to have properties differing from those associated with the materials selected for the flexible body 282. For example, the support insert 286 can be formed to create desired mechanical properties in the annuloplasty prosthesis 280, such as enhanced lateral support when applied to a heart valve annulus (not shown). However, the support insert 286 is not a rigid stiffening member otherwise employed with conventional, rigid, annuloplasty products, such that the annuloplasty prosthesis 280 remains flexible. For example, in one embodiment, the support insert 286 is silicone rubber, although other materials, such as woven polyester, polymeric materials, etc., are also acceptable.

Assembly of the annuloplasty prosthesis 280 is straightforward, with the support insert 286 being inserted within the interior region 304 of the tubular flexible body 282. As with previous embodiments, the annuloplasty prosthesis 280 is substantially rectangular in transverse cross-section upon final assembly. To this end, one or more stitch lines 306 can be employed to secure the flexible body 282 and the support insert 286 to one another, as well as to ensure the desired final shape is maintained. With this in mind, the annuloplasty prosthesis 280 is configured to adequately support a heart valve annulus (not shown) in a manner commensurate with currently available products, yet has a nominal height H of not more than 2.5 mm, more preferably not more than 2.3 mm. In some embodiments, the annuloplasty prosthesis 280 has a nominal width W greater than the height, with the width W being not more than 5.0 mm, more preferably not more than 4.5 mm. Finally, in some embodiments, the annuloplasty prosthesis 280 preferably exhibits a Force-Displacement Slope Average Value of not less than 10.0 lbs/in over the first 1 mm of compression, more preferably not less than 10.5 lbs/in over the first 1 mm of compression, even more preferably not less than 11.0 lbs/in over the first 1 mm of compression.

Figure 8:
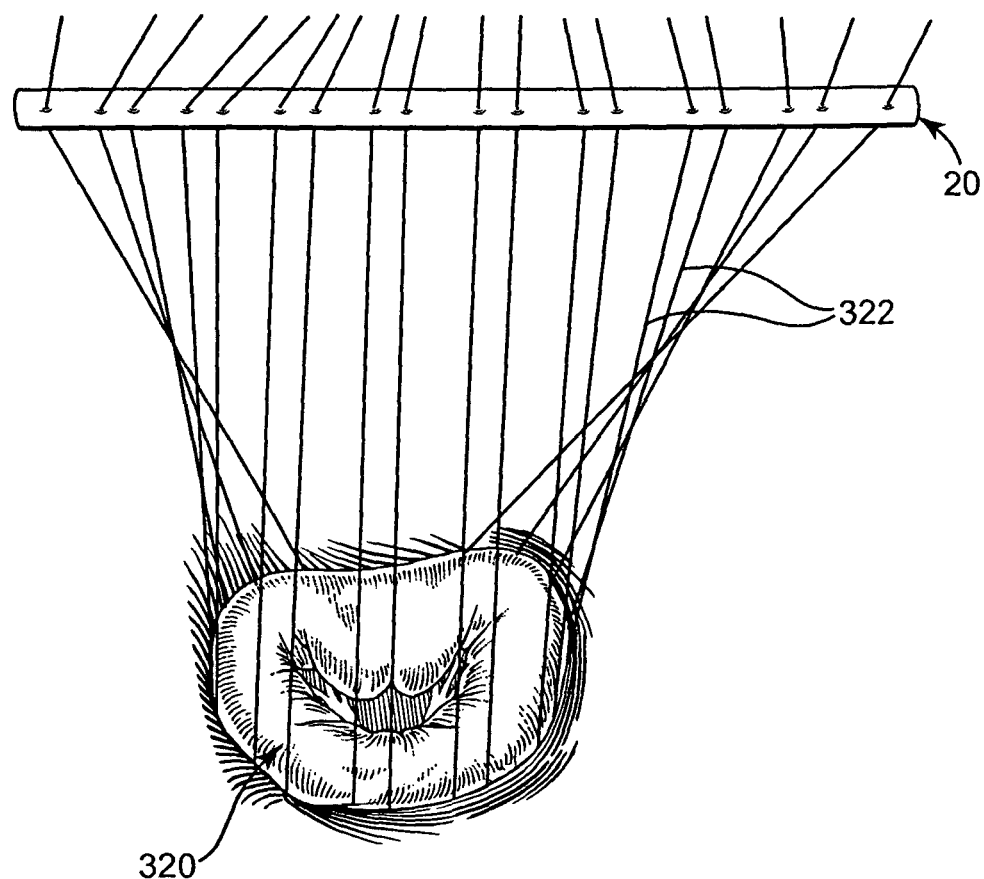
FIGS. 8 and 9 illustrate one method of implanting a flexible annuloplasty prosthesis provided in accordance with principles of the present invention.

As indicated by the above, the flexible annuloplasty prosthesis in accordance with principles of the present invention can assume a wide variety of forms. Similarly, a variety of techniques can be employed to implant the flexible annuloplasty prostheses of the present invention. For example, FIG. 8 illustrates the flexible annuloplasty prosthesis 20 in band form, being implanted to a heart valve annulus 320. Sutures 322 are first sutured or connected to tissue of the annulus 320, and then connected to the annuloplasty prosthesis 20. In this regard, the annuloplasty prosthesis 20 is maintained at a short distance from the annulus 320, such as with a holding device (not shown). Because the annuloplasty prosthesis 20 is flexible, it can be retained in the linear or straight shape shown in FIG. 8 while the sutures 322 are being connected to the annulus 320 and the annuloplasty prosthesis 20. The sutures 322 can all be first sutured to the annulus 320 and then secured to the prosthesis 20; alternatively, sutures 322 can consecutively be threaded through the annulus 320 and the prosthesis 20 on an individual basis. Regardless, due to the above-described low profile characteristic of the annuloplasty prosthesis 20, the annuloplasty prosthesis 20 presents only a minimal obstruction to a surgeon's view of the annulus 320 as the sutures 322 are applied. Further, the substantially rectangular transverse cross-sectional shape of the annuloplasty prosthesis 20, in accordance with one embodiment, allows the surgeon to readily identify a proper location of the sutures 322 relative to the annuloplasty prosthesis 20. Once all of the sutures 322 have been secured to the annuloplasty prosthesis 20, the prosthesis 20 is removed from the holding device.

Figure 9:
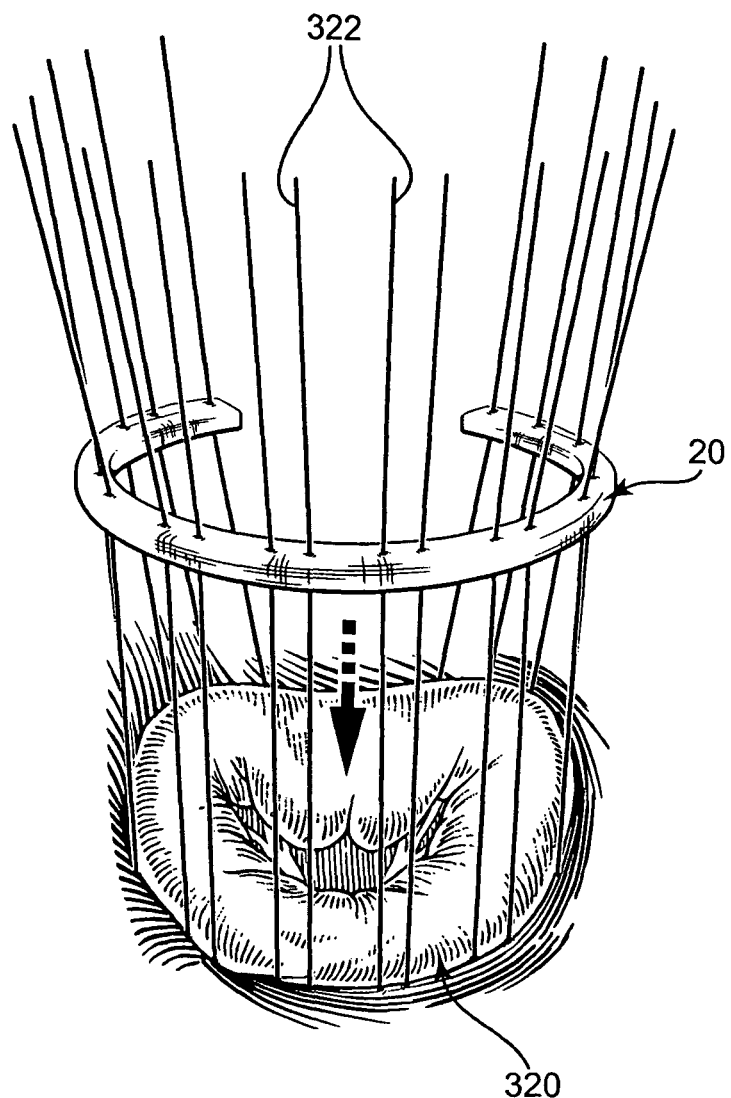
Figure 10:
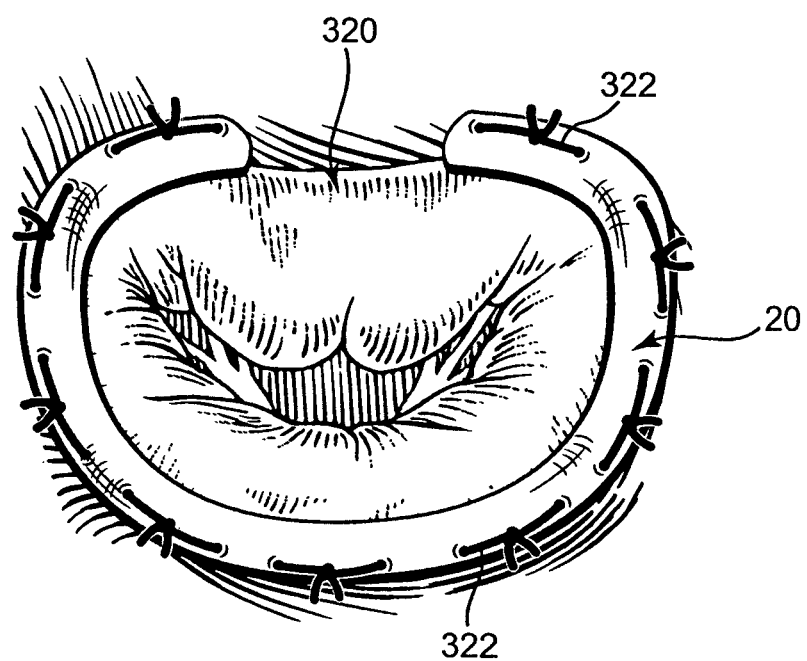
FIG. 10 is a perspective view of a flexible annuloplasty prosthesis in accordance with principles of the present invention implanted to a heart valve annulus.

Subsequently, and with reference to FIG. 9, the annuloplasty prosthesis 20 is directed or slid toward the annulus 320 along the sutures 322. The sutures 322 force the annuloplasty prosthesis 20 to mimic the curvilinear shape of the annulus 320 as the annuloplasty prosthesis 20 is directed toward the annulus 320. Finally, as shown in FIG. 10, the annuloplasty prosthesis 20 is placed or implanted against the annulus 320, and the sutures 322 are knotted so as to prevent movement of the annuloplasty prosthesis 20 from the annulus 320. Notably, due to the enhanced longitudinal stiffness associated with one embodiment of the present invention, the annuloplasty prosthesis 20 does not buckle or deform at any of the suture pairs 322 that otherwise impart a longitudinal force (e.g., a longitudinally compressive force) onto the annuloplasty prosthesis 20. The methodology associated with FIGS. 8-10 can be employed to implant any of the flexible annuloplasty prostheses previously described.

The following example and comparative example further describe the flexible annuloplasty prosthesis in accordance with principles of the present invention and the tests performed to determine characteristics of the annuloplasty prosthesis. The examples are provided for exemplary purposes to facilitate an understanding of the invention, and should not be construed to limit the invention to the examples.

EXAMPLES

Multiple flexible annuloplasty prosthesis in the form of annuloplasty bands were formed in accordance with FIGS. 2A and 2B. In particular, a polyester double velour material (Advantage 166611 Meadox double velour from Boston Scientific of Boston, Mass.) was folded in the manner shown in FIG. 2B. A silicone radiopaque marker (0.020 inch in height) was disposed within the folded material. A pair of 4-0 sutures were sewn through the folded material. The resultant flexible annuloplasty band had a height of approximately 2.3 mm and a width of approximately 4.0 mm. The flexible annuloplasty bands were implanted by an experienced surgeon to multiple different animal heart valve annuli and evaluated. It was determined that the flexible annuloplasty bands fully supported the annular tissue in a manner consistent with currently sold flexible annuloplasty prosthesis.

Another similarly-formed, flexible, annuloplasty prosthesis was subjected to the Force-Displacement Slope Average Value test described above. The flexible annuloplasty prosthesis exhibited a Force-Displacement Slope Average Value of approximately 11.5 lbs/in over the first 1 mm of compression. By way of comparison, available flexible annuloplasty prostheses sold under the trade name Cosgrove-Edwards from Edwards of Irvine, Calif., were tested and found to have a Force-Displacement Slope Average Value of approximately 9.0 lbs/in over the first 1 mm of compression. Thus, as compared to existing flexible annuloplasty products, the annuloplasty prosthesis in accordance with embodiments of the present invention is longitudinally stiffer and thus more readily resists longitudinally buckling or displacement in response to a longitudinal force.

Although the present invention has been described with reference to preferred embodiments, workers skilled in the art will recognize that changes can be made in form and detail without departing from the spirit and scope of the present invention. For example, any of the flexible annuloplasty prostheses described herein can be provided in either band or ring form.

What is claimed is:

1. A flexible annuloplasty prosthesis for repairing a heart valve having a valve annulus, the annuloplasty prosthesis comprising:
    a flexible body defining an exterior of the prosthesis, the flexible body formed of a biocompatible fabric material folded onto itself and configured to rest against and support a heart valve annulus upon implantation, the folded fabric material forming opposing first and second major exterior surfaces and opposing first and second exterior sides, and including, in transverse cross-section:
    a first layer defining the first major exterior surface,
    a second layer defining the second major exterior surface,
    a third layer positioned between, and oriented substantially parallel to, the first and second layers,
    a fourth layer positioned between, and oriented substantially parallel to, the second and third layers,
    a fifth layer positioned between, and oriented substantially parallel to, the second and fourth layers, wherein the folded fabric material forms a first fold segment interconnecting the first and second layers defines one of the opposing first and second exterior sides, the folded fabric material forms a second fold segment interconnecting the first and third layers, the folded fabric material forms a third fold segment interconnecting the second and fourth layers, the second and third fold segments combining to define another of the opposing first and second exterior sides, and the folded fabric material forms a fourth fold segment interconnecting the fourth and fifth layers, further wherein the first and second layers are transversely spaced apart to define a region therebetween, and wherein the region is further defined between the first and fourth fold segments; and
    stitching along a length of the flexible body and through a height of the flexible body to compressively secure the layers to one another, the stitching including a first continuous stitch and a second continuous stitch, the first and second continuous stitches being laterally spaced from one another along the length of the flexible body, the first continuous stitch extending through each of the first major exterior surface, the first layer, the second layer, the third layer, the region, and the second major exterior surface, the second continuous stitch extending through each of the first major exterior surface, the first layer, the second layer, the third layer, the fourth layer, the fifth layer, and the second major exterior surface.

2. The annuloplasty prosthesis of claim 1, wherein the annuloplasty prosthesis is configured such that the first major exterior surface intimately contacts annular tissue upon implantation, and further wherein the height is defined as a dimension from the first major exterior surface to the second major exterior surface.

3. The annuloplasty prosthesis of claim 1, wherein the annuloplasty prosthesis is configured such that the first major exterior surface intimately contacts annular tissue upon implantation, the height being defined as a dimension between the opposing first and second major exterior surfaces and the width being defined as a dimension between the opposing first and second exterior sides.

4. The annuloplasty prosthesis of claim 1, wherein the annuloplasty prosthesis has a height of not more than 2.3 mm.

5. The annuloplasty prosthesis of claim 1, wherein the annuloplasty prosthesis is characterized by the absence of a metal stiffening member extending within the flexible body.

6. The annuloplasty prosthesis of claim 1, wherein the annuloplasty prosthesis exhibits a Force-Displacement Slope Average Value of not less than 10.0 lbs/in over a first 1 mm of compression.

7. The annuloplasty prosthesis of claim 6, wherein the annuloplasty prosthesis exhibits a Force-Displacement Slope Average Value of not less than 10.5 lbs/in over a first 1 mm of compression.

8. The annuloplasty prosthesis of claim 1, wherein the annuloplasty prosthesis has a width of not more than 5.0 mm.

9. The annuloplasty prosthesis of claim 8, wherein the annuloplasty prosthesis is configured such that the first major exterior surface intimately contacts annular tissue upon implantation, the height being defined as a dimension between the opposing first and second major exterior surfaces and the width being defined as a dimension between the opposing first and second exterior sides.

10. The annuloplasty prosthesis of claim 1, wherein the annuloplasty prosthesis is substantially rectangular in transverse cross-section.

11. The annuloplasty prosthesis of claim 1, further comprising:
    a radiopaque marker contained within the region of the folded fabric material.

12. The annuloplasty prosthesis of claim 11, wherein the first continuous stitch extends through the radiopaque marker to secure the radiopaque marker relative to the flexible body.

13. The annuloplasty prosthesis claim 1, wherein the biocompatible fabric material is a double velour material.

14. The annuloplasty prosthesis of claim 1, wherein the annuloplasty prosthesis is a band.

15. The annuloplasty prosthesis of claim 1, wherein the annuloplasty prosthesis is a ring.

16. The annuloplasty prosthesis of claim 1, wherein the flexible body has sutures to secure the flexible body to the heart valve annulus upon implantation, the sutures being separate from the first stitch and the second stitch.

17. The annuloplasty prosthesis of claim 1, further comprising a third stitch to connect the second and third fold segments.

18. The annuloplasty prosthesis of claim 1, wherein the first continuous stitch is adjacent the first fold segment and the second continuous stitch is adjacent the second and third fold segments.

19. The annuloplasty prosthesis of claim 1, wherein the stitching directly restrains the annuloplasty prosthesis to a maximum nominal height of not more than 2.5 mm.

* * * * *